Figure 1:
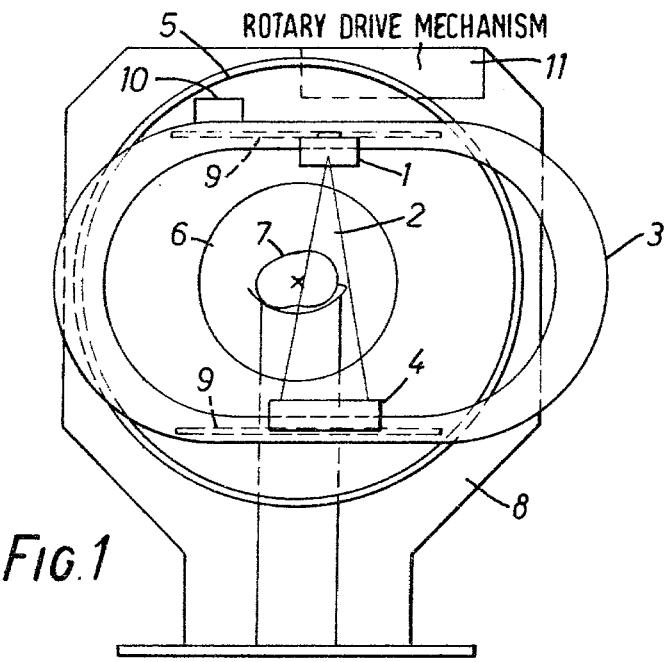

United States Patent [19]

Lodge

[11] 4,250,761
[45] Feb. 17, 1981

[54] ROTARY DRIVE MECHANISMS

[75] Inventor: James A. Lodge, Maidenhead, England

[73] Assignee: E M I Limited, Middlesex, England

[21] Appl. No.: 890,675

[22] Filed: Mar. 27, 1978

[30] Foreign Application Priority Data

Apr. 13, 1977 [GB] United Kingdom ............... 15259/77

[51] Int. Cl.³ ............................................. F16H 27/04
[52] U.S. Cl. ..................... 74/84 R; 74/112; 74/128; 74/813 R; 74/825
[58] Field of Search .................... 74/88, 111, 112, 113, 74/84, 128, 574, 813 R, 813 C, 816, 817, 821, 822, 825

[56] References Cited

U.S. PATENT DOCUMENTS

| 1,303,725 | 5/1919 | Rhine | 173/162 X |
|---|---|---|---|
| 2,209,858 | 7/1940 | Steiert | 74/112 |
| 2,685,822 | 8/1954 | Walton | 74/574 X |
| 3,120,134 | 2/1964 | Sweeney | 74/813 X |
| 3,236,122 | 2/1966 | Biernson | 74/825 |
| 3,518,899 | 7/1970 | Greenberg et al. | 74/825 X |
| 3,749,372 | 7/1973 | Funk | 74/574 X |
| 3,778,614 | 12/1973 | Hounsfield | 250/362 |
| 3,782,506 | 1/1974 | Yarrington | 74/574 X |
| 3,946,234 | 3/1976 | Hounsfield | 250/363 S |

Primary Examiner—Lawrence J. Staab
Attorney, Agent, or Firm—Cooper, Dunham, Clark, Griffin & Moran

[57] ABSTRACT

In computerized tomographic apparatus having an intermittent rotational motion the scanning time can be reduced by increasing the rotation speed. However this can result in excessive forces being transmitted to the stationary mainframe of the equipment. The invention reduces that problem by balancing the forces of rotation at least in part by appropriately placed counter masses. In one embodiment the counter masses rotate and properly balance the forces. In another embodiment they move linearly and delay the application of the forces to the mainframe and transmit the delayed forces over a longer period.

16 Claims, 5 Drawing Figures

ROTARY DRIVE MECHANISM

ROTARY DRIVE MECHANISMS

The present invention relates to rotary drive mechanisms and relates especially, though not exclusively, to such mechanisms for use in rotating a source of penetrating radiation, such as X-radiation, in steps around a body, in the course of a computerised tomographic (CAT) examination of the body.

Examples of apparatus for computerised tomographic examination are described, for example, in U.S. Pat. No. 3,778,614, and in one example described therein a source, of a single pencil-like beam of the radiation, is scanned laterally across a slice of the body in alternation with a small angular movement of, say, $\frac{1}{2}°$ of 1°, around the body. The motion of the source is followed by a detector, placed on the opposite side of the body to the source, so that the absorption suffered by the radiation, on traversing each of many beam paths through the body, can be determined. The absorption values so determined are processed to provide a representation of the absorption coefficient, with respect to said radiation, at each of many small locations distributed over the slice.

It is desirable in some circumstances for the absorption values to be acquired more rapidly than they can be when using the kind of apparatus using a single beam of radiation. It has been disclosed in the Specification of U.S. Pat. No. 3,946,234, that it is possible to replace the aforementioned single beam of radiation with a fan-shaped distribution of radiation subtending an angle of, for examle, 10° and by distributing an array of, say, thirty detectors across the breadth of the distribution, and scanning the source and detectors laterally across the slice, to cause each of the detectors to provide a respective series of signals relating to a respective set of parallel beam paths through the body during one scan. The angular movements can thus be made through steps of 10° (in this example) and thus the scanning may be effected much more rapidly than in the case previously described, in which a single beam is used whilst maintaining dosage levels and signal-to-noise ratios of the absorption values substantially unchanged. A typical scan time for a CAT apparatus using a 10° distribution of radiation, as described in this paragraph, is twenty seconds (EMI-Scanner computerised tomographic system Model CT 5005).

Requirements exist for even faster scan times, however, and since the aforementioned scanning technique has proved to be reliable in practic, it is desirable to utilise the same technique suitably modified to effect the faster scanning. Prima facie, it would appear straightforward to speed up the scanning described in the preceding paragraph by extending the fan angle of the spread of radiation and performing angular movements through the new, larger, angle. Indeed, in the example of the invention to be described hereinafter, the fan angle and the angular movements are both extended to typically 20°. However, difficulty can arise in some circumstances due to excessive torques which can be generated in moving the relatively massive source and detectors on a scanning gantry rapidly through an angle such as 20°.

Arrangements have been proposed in U.S. Application Ser. No. 856,603, for reducing the effect of such torques. It is an object of this invention to provide an alternative to such arrangements.

According to the present invention there is provided a rotary drive system, arranged to provide an intermittent rotation of a rotatable member, about an axis, relative to a fixed frame of reference, the system including: at least one drive member including two parts and a mounting which allows each part to be capable of motion relative to the fixed frame of reference and capable of motion relative to the other part; coupling means for engaging the rotatable member, attached to a first of the parts; and a countermass, attached to the second part; the total moments of inertia of, on the one hand, the rotatable member including equipment mounted thereon, and, on the other hand, the at least one countermass being related such that, on relative motion of the two parts with the coupling means engaged with the rotatable member, the rotatable member and the at least one countermass are imparted with opposing motions relative to the fixed frame of reference.

In one embodiment of the invention, the relative motions are linear and means are provided to hold the rotary member in a fixed position while, with the means for engaging disengaged, the relative linear motions are reversed to an initial position.

Figure 2:
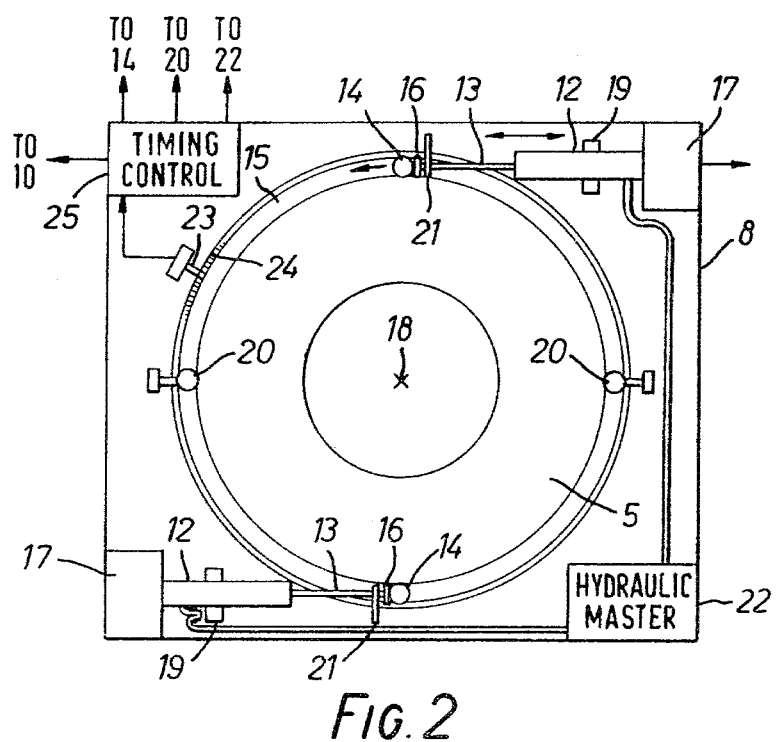
Figure 3:
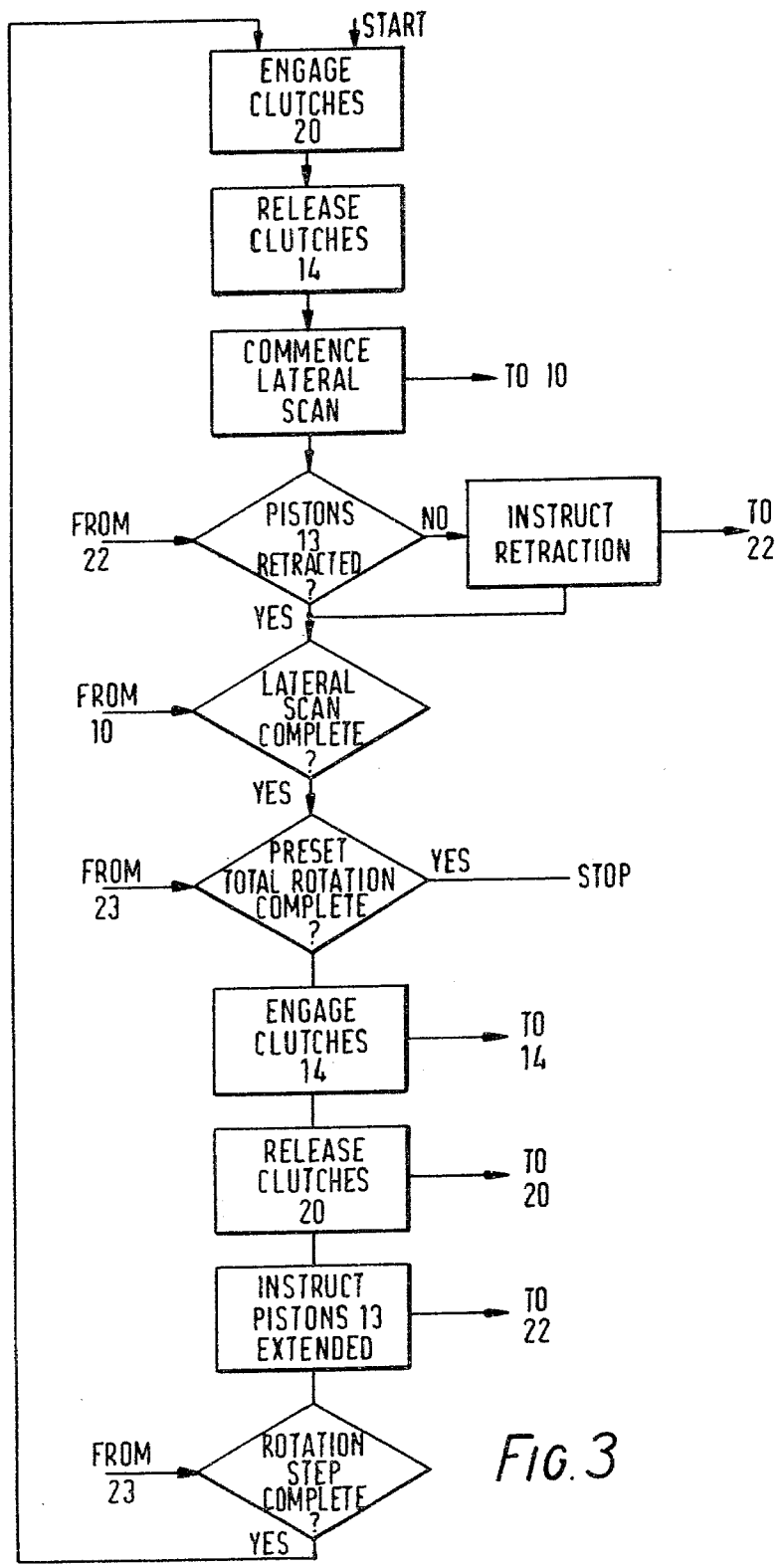
Figure 4:
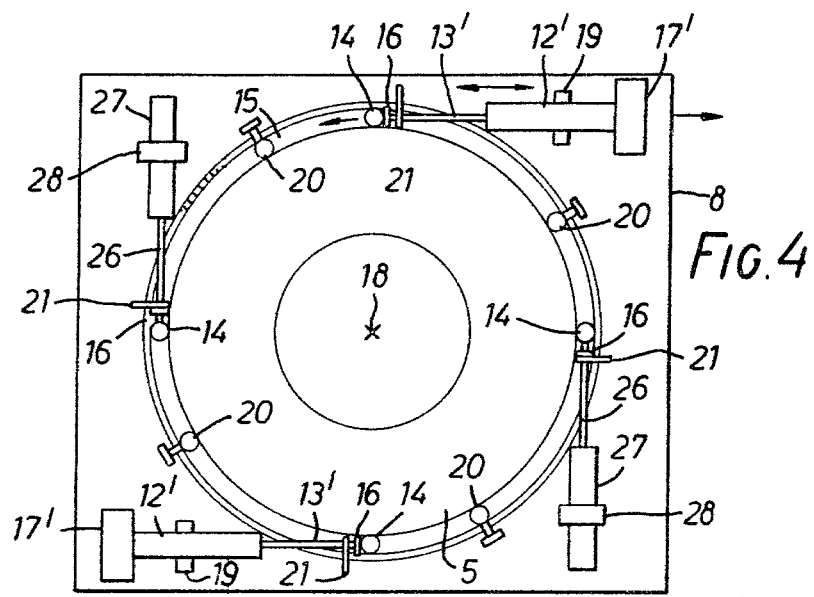
Figure 5:
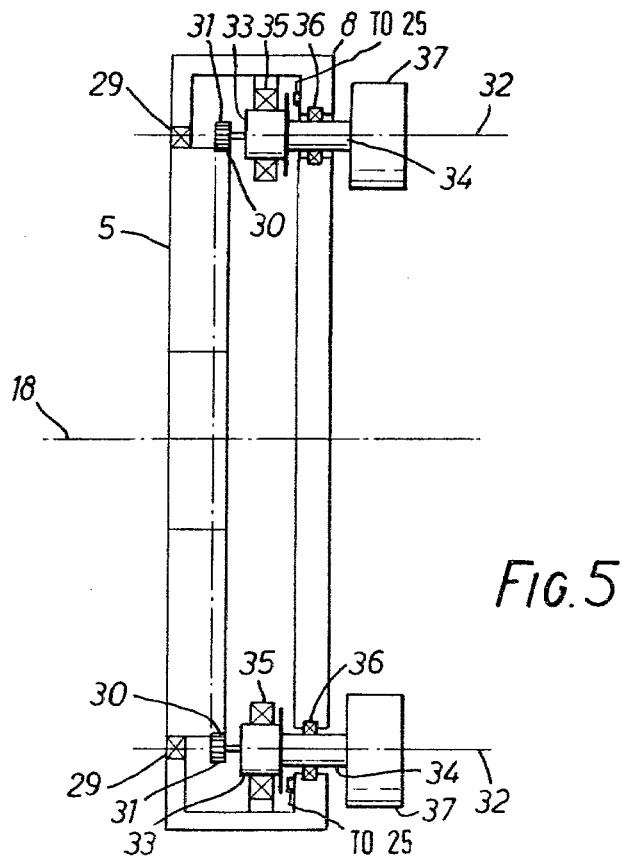

In order that the invention may be clearly understood and readily carried into effect, examples will now be described with reference to the accompanying drawings of which:

FIG. 1 shows in simplified form a CAT apparatus suitable for using the invention, FIG. 2 shows an example of the invention using relative linear motion, FIG. 3 is a flow chart illustrating the operational sequence of the FIG. 2 arrangement, FIG. 4 shows a modification of FIG. 2 employing more hydraulic rams to delay only part of the forces, and FIG. 5 shows an alternative example using relative rotational motion.

There is shown in FIG. 1 a simplified form of the apparatus disclosed in U.S. Pat. No. 3,946,234. A source 1, of a fan-shaped distribution 2 of X-rays, is mounted on a yoke 3. A detector unit 4, comprising a plurality of detectors, is also mounted on yoke 3 to intercept the radiation.

A rotatable member 5, having an aperture 6 in which the body 7 of a patient can be inserted, is mounted on bearings, not shown in this figure, on a fixed main frame 8. Member 5 carries tracks 9 on which yoke 3 can move laterally. A motor 10 is provided to reciprocate the yoke, and hence the source 1 and detectors 4, to scan radiation 2 across the body 7. As mentioned a rotary motion, of source 1 about the body 7, is also desired. For that purpose a mechanism 11 is provided to rotate member 5, and the equipment mounted thereon, in steps alternating with the lateral scans. One mechanism 11 has been shown as a block but, of course, two or more may be used to provide a balanced drive. It is the form of this mechanism 11 which is the subject of this invention.

One example of a mechanism 11, in accordance with this invention, is shown in FIG. 2. Two units are shown, each comprising a hydraulic ram or actuator, with cylinder 12 and piston 13. At the end of the piston there is carried a friction clutch 14 engageable with a friction surface 15 on member 5. Although a single clutch pad is shown, it is preferable to provide two parts gripping opposite sides of member 5. Piston 13 also carries a stop 16. Cylinder 12 carries a mass 17 having a moment of inertia about the rotational axis 18, of member 5, equivalent to the moment of inertia about that axis of member 5 itself, with equipment mounted thereon. The cylinder is also mounted on bearings 19 allowing motion, relative to main frame 8, in the direction of motion of the piston 13. Two further clutches 20 are also capable of gripping surface 15 but are rigidly fixed to mainframe 8. Mainframe 8 also carries stops 21 arranged to engage stops 16 to limit motion, in one direction of clutches 14. Also included is a hydraulic unit, indicated generally at 22, which includes a hydraulic master cylinder operating both pistons 13. The master cylinder may be controlled in any suitable manner.

The arrangement shown in FIG. 2 is intended to provide an anti-clockwise stepped motion of member 5, as viewed in the Figure. In operation clutches 14 are engaged with surface 15, while clutches 20 are released. Pistons 13 are extended to move clutches 14 in the anti-clockwise direction. Although the motion is small, about 20°, it should be realised that the motion is a rotational one and therefore the pistons and associated components should be capable of allowing that motion. Since the moments of inertia of masses 17 and cylinders 12 are substantially equal to those of the member 5 and associated components, the pistons 13 and cylinders 12 make substantially equal and opposite motions. Thus at the end of the rotational step masses 17 have been moved in an outward direction as shown by the arrows. The clutches 20 are then engaged to hold member 5 during the next lateral scan of the source 1, and clutches 14 released.

In the time taken for the lateral scan the pistons 13 are returned to their initial position. In view of the large masses 17 the cylinders tend to remain stationary as the pistons retract. However, when clutches 14 reach the starting position, stops 16 engage fixed stops 21 and further retraction of the piston pulls the cylinders 12 and masses 17 back to their starting position. The equipment is then ready to repeat the rotational step.

Clearly, during the rotation step there is no transfer of forces to main frame 8, in view of the equal and opposite motion of the equal moment of inertia masses. However, on retraction, as stops 16 and 21 engage, the forces to retract masses 17 are transmitted to mainframe 8 via stops 21. This is merely a delayed transfer of the rotational forces. Nevertheless, this transfer can be made over a relatively long period during the lateral scan, compared with the fast rotational step.

Preferably, means should be provided to accurately control the extent of each angular step; for example, by holding member 5 as it reaches the desired position before piston 13 has completed its stroke, In one example, such means may comprise a photocell and associated light source 23 co-operating with a graticule 24 formed on the circumference of member 5. Such a photocell unit provides output pulses as its light path is broken by lines on the transparent graticule substrate. These pulses, which indicate the progress of the rotation, are applied to a timing control unit 24 which, in turn, sends signal to engage clutches 20 after the desired rotational movement, and also to motor 10 to control the lateral scan of the source. Control unit 24 also sends signals to clutches 14 and hydraulic master unit 22 to control the operation of cylinders 12 and receives, in turn, signals from unit 22 indicating the positions of the cylinders 12.

The construction of circuits for unit 25 will be apparent to those skilled in the art, since the circuits are merely required to respond to preset inputs to initiate a further action. In order to illustrate the form which these actions can take, FIG. 3 shows one example of a flow diagram showing a suitable sequencing, as described hereinbefore, to operate the equipment of FIG. 2. The diagram requires inputs in the form of timing pulses or position signals from motor 10, photocell unit 23 and hydraulic master unit 22, and provides control signals to motor 10, clutches 14 and 20 and hydraulic master unit 22. The circuits are preset to a total rotation required, which should preferably be at least 180° and may be 360°, and count pulses from photocell 23 until the total count indicates that the total rotation is complete; at which stage the examination is terminated. Other holding mechanisms, such as a hydraulic actuated pin, engaging one of a series of holes at the circumference of 5, can be used to replace clutches 14.

It has been mentioned that the arrangement of FIG. 1 transfers reaction forces to the main frame 8, although delayed and over a longer period. Of course, it is still advantageous if only a part of the reaction forces is so delayed, part still being transferred directly. This is possible if the masses 17 have a moment of inertia which is a substantial proportion of that of member 5, i.e. a large enough proportion to delay a detectable part of the force. Part of the force can be transmitted directly by a more conventional drive and this part should be small enough to not transmit excessive forces for the structure used. A convenient proportion would be half, but it may be more or less. A further development to achieve that effect is shown in FIG. 4, and it includes four hydraulic rams. Two, 12', 13', are similar to 12/13 of FIG. 1, but with total masses 17' having half of the moment of inertia of the rotating parts, and two, comprising pistons 26 and cylinders 27, react directly against main frame 8 being fixed thereto at 28 to allow only a necessary rotational movement. All four are engaged simultaneously to provide the rotation step, the sequencing being eventually the same as for FIGS. 2, 3. The two additional rams 26, 27, transfer half the reaction forces directly to the main frame during the rotation while the other two 12', 13', transfer the remaining half of the forces during the lateral scan. Other combinations can, of course, be used.

An alternative arrangement is shown in a side elevation in FIG. 5. Rotary member 5 is mounted in bearings 29 fixed to main frame 8, as in the arrangement of the earlier Figures, although it can only be clearly seen in the side elevation. In this arrangement, circumference of member 5 is provided with gear teeth at 30 which can be driven by one or more gear wheels 31 rotating about respective axes 32. Each gear wheel is fixed to the 'stator', in this case rigidly attached to the casing, of a respective motor 33. The 'stator' and an extension 34 of the 'rotor' of each motor are mounted on mainframe 8 on respective bearings 35 and 36 so that each is capable of rotating about its axis 32. The rotor also carries a mass 37; the arrangement being such that the total masses of all such motors have moments of inertia substantially equal to the amount of inertia of member 5 and associated parts.

In operation, as each 'stator' rotates to drive member 5 via the respective gear wheel 31, the rotor and mass 37 have an equal and opposite rotation to the stator to absorb forces of reaction. Unlike the linear system this arrangement does not need to be returned to a starting position. As for the FIGS. 2 and 4 arrangement, means are provided to accurately determine the extent of rotation. Such means may be as described hereinbefore or by making at least one of motors 28 a servo or stepping motor.

The motors 28 are supplied via slip rings 38 mounted on the motor casing and co-operating brushes 39 mounted on mainframe 8. These may take conventional form. By these means, control signals are carried to and from motors 28 and timing control unit 25. The operation of the FIG. 5 arrangement is essentially as described for FIG. 2, except for the lack of a return motion of the compensating masses and other modifications consequent on the replacement of hydraulic rams with motors 28. Other possible arrangements operating the counter mass principle may be devised by those skilled in the art.

What I claim is:

1. A rotary drive system, arranged to provide an intermittent rotation of a rotatable member, about an axis, relative to a fixed member, the system including: at least one drive member including two parts and means for mounting which allows each part to be capable of motion relative to the fixed member and capable of motion relative to the other part; coupling means, for engaging the rotatable member, attached to a first of the parts; and a countermass, attached to the second part; the total moments of inertia of, on the one hand, the rotatable member, including equipment mounted thereon, and, on the other hand, the countermass of said at least one drive member being related such that, on relative motion of the two parts with the coupling means engaged with the rotatable member, the rotatable member is imparted with a motion relative to the fixed member, substantially without transfer of reactive force from the drive member to said fixed member, while the countermass of said at least one drive member is imparted with an opposing motion thereto.

2. A rotary drive system according to claim 1 in which the total moment of inertia of the countermass of said at least one drive member is substantially equal to the total moment of inertia of the rotatable member.

3. A rotary drive system according to claim 1 in which the moment of inertia of each countermass is a substantial proportion of the total moment of inertia of the rotatable member.

4. A rotary drive system according to claim 3 in which the moment of inertia of each countermass is substantially half that of the rotatable member.

5. A rotary drive system according to claim 1 in which there are two of said first mentioned drive members.

6. A rotary drive system according to claim 1 in which the relative motion of the two parts of the at least one drive member is substantially linear, the means for engaging and mounting being such that the linear motion of the first part can be transmitted to the rotatable member as said rotary motion.

7. A rotary drive system according to claim 6 in which the means for engaging includes at least one clutch.

8. A rotary drive system according to claim 6 in which the at least one drive member is at least one hydraulic ram.

9. A rotary drive system according to claim 8 in which the one part of the at least one drive member is the piston of the at least one ram and the second part is the cylinder.

10. A rotary drive system according to claim 6 incuding: means for holding the rotatable member in a fixed position relative to the fixed member; and means for controlling the means for holding and the means for engaging such that the rotatable member is free to rotate and is driven by the at least one drive member during linear motion in one direction and is prevented from rotation and disengaged from the at least one drive member during linear motion of the at least one drive member in the reverse direction.

11. A rotary drive system according to claim 10 in which the means for holding is at least one clutch.

12. A rotary drive system according to claim 1 wherein the relative motion is rotational.

13. A rotary drive system according to claim 1 wherein the at least one driving means is an electric motor including a stator forming one of said parts and a rotor forming the other.

14. A rotary drive system according to claim 13 in which the stator is the first of said parts and the rotor is the second.

15. A rotary drive system according to claim 13 in which the axes of rotation of the motor are parallel to the axis of rotation of the rotatable member.

16. A rotary drive system according to either claim 3 or claim 4 in which at least one additional drive member is provided, fixed in relation to the fixed member.

* * * * *